(12) United States Patent
Doty

(10) Patent No.: US 8,202,557 B1
(45) Date of Patent: Jun. 19, 2012

(54) BIO-PESTICIDE AND METHODS OF MAKING AND USING THE SAME

(76) Inventor: Sundy Aisha Doty, Port Clinton, OH (US)

( * ) Notice: Subject to any disclaimer, the term of this patent is extended or adjusted under 35 U.S.C. 154(b) by 400 days.

(21) Appl. No.: 12/365,841

(22) Filed: Feb. 4, 2009

Related U.S. Application Data

(60) Provisional application No. 61/006,876, filed on Feb. 5, 2008.

(51) Int. Cl.
*A61K 36/67* (2006.01)
(52) U.S. Cl. .................................................... 424/734
(58) Field of Classification Search .................. None
See application file for complete search history.

(56) References Cited

U.S. PATENT DOCUMENTS

| | | | |
|---|---|---|---|
| 5,106,622 A | | 4/1992 | Sherwood et al. |
| 5,435,821 A | | 7/1995 | Duvdevani et al. |
| 5,466,459 A | * | 11/1995 | Wilson .......................... 424/407 |
| 5,747,056 A | | 5/1998 | Potter et al. |
| 5,756,100 A | | 5/1998 | Martinez |
| 5,839,224 A | | 11/1998 | Emerson et al. |
| 6,048,714 A | | 4/2000 | Hiromoto |
| 6,183,767 B1 | | 2/2001 | Bessette et al. |
| 6,523,298 B2 | | 2/2003 | Neumann |
| 6,593,299 B1 | | 7/2003 | Bennett et al. |
| 6,750,256 B1 | | 6/2004 | Crandall, Jr. et al. |
| 6,855,351 B2 | | 2/2005 | Ramarethinam |
| 6,925,751 B2 | | 8/2005 | Williams et al. |
| 7,019,036 B2 | | 3/2006 | Hiromoto |
| 7,029,687 B1 | | 4/2006 | Joiner |
| 2006/0269626 A1 | * | 11/2006 | Martinez et al. .............. 424/757 |

FOREIGN PATENT DOCUMENTS

| | | | |
|---|---|---|---|
| CN | 1337243 A | * | 2/2002 |
| DE | 4327792 A1 | * | 4/1995 |
| JP | 77017099 B | * | 5/1977 |
| JP | 08295601 A | * | 11/1996 |
| WO | WO 0201959 A1 | * | 1/2002 |

* cited by examiner

*Primary Examiner* — Amy L Clark
(74) *Attorney, Agent, or Firm* — Brannen Law Office, LLC

(57) ABSTRACT

The present invention relates to a bio-pesticide comprising a mixture of natural spices that kills insects through direct contact. *Piper Nigrum, Cuminum Cyminum, Cinnamomum Verum, Allium Sativum, Coriandrum Sativum, Curcuma, Foeniculum Vulgare, Trigonella Foenum Graecum, Syzygium Aromaticum, Capsicum, Zingiber Officinale, Murraya Koenigii, Brassica Nigra*, and Sodium Chloride are mixed with potting soil and applied to a plant. The bio-pesticide works through the processes of repellency, digestive inhabitancy, paralysis and suffocation. The bio-pesticide can be applied as a dust or liquid spray to the plants, and can eliminate the pests within 48-72 hours.

4 Claims, No Drawings

BIO-PESTICIDE AND METHODS OF MAKING AND USING THE SAME

This application claims priority on and the benefit of provisional application 61/006,876, filed Feb. 5, 2008, which remains currently pending, the entire contents of which are hereby incorporated herein by reference.

BACKGROUND OF THE INVENTION

1. Field of the Invention

The present invention relates to a bio-pesticide comprising a mixture of natural spices that kills insects through direct contact and that is easily applied.

2. Description of the Related Art

The United States Environmental Protection Agency (the "US EPA") defines a pesticide as any substance or mixture of substances intended for preventing, destroying, repelling, or mitigating any pest. The US EPA further states that the term pesticide is often misunderstood to refer only to insecticides. However, the term pesticide also applies to herbicides, fungicides, and various other substances used to control pests. Further, the US EPA has stated that a pesticide is also any substance or mixture of substances intended for use as a plant regulator, defoliant, or desiccant.

The US EPA defines pests as being living organisms that occur where they are not wanted or that cause damage to crops or humans or other animals. Examples include: insects, mice and other animals, unwanted plants (weeds), fungi, microorganisms such as bacteria and viruses, and prions. Examples of damage include competing with humans for food, destruction of property, the spread or disease and being a nuisance.

Many pesticides are effective at destroying pests, but are also toxic to humans or other unintended animals. Pests also are capable of becoming resistant to certain pesticides. In this regard, there is a well known need to find effective pesticides that are non-toxic to humans. Humans have been seeking new pesticides since about 4,500 years ago when elemental sulfur dusting was first used in Sumeria.

Many events occur during the process of discovering and developing a new pesticide. The desirable quantities are optimized through empirical and field testing. This process is more challenging with the optimization of bio-pesticides. Among the reasons for this complexity is that the natural ingredients can have variable amounts of active and inactive compounds.

Once the structures and processes of the ingredients are known, the toxicological and environmental properties of the compound must be considered. Being safe and being naturally occurring are not necessarily synonymous. It is known that some of the most toxic mammalian poisons are natural products and many of these are plant products. Some have defined the toxicity as being both a function of quality (i.e. the relative harmfulness of a compound) and of quantity (i.e. the amount of exposure).

Given the continual increased production demands we as a society place on any given area of land, it is easily understandable why pesticides with increased effectiveness and decreased undesirable impacts are sought. This is true not only of traditional commercial farms, but also of personal gardens.

It may be helpful to review briefly a few issued United States patents to illustrate some products and methods of delivery that have been developed over the years. United States Patent Number (hereafter, "USPN") U.S. Pat. No. 5,106,622 to Sherwood et al. is titled Repellent Composition Containing Natural Oils of Citronella, Cedar and Wintergreen and Use Thereof. This patent illustrates the use of natural oils mixed in equal amounts that are claimed to be an environmentally safe topical pest control.

U.S. Pat. No. 5,435,821 to Duvdevani et al. is titled Controlled Release Vegetation Enhancement Agents Coated with Sulfonated Polymers, Method of Production and Processes of Use. This patent describes the use of a pesticide within a broader system attempting to enhance growth of vegetable matter.

U.S. Pat. No. 5,747,056 to Potter et al. is titled Pesticide Compositions Containing Mustard Bran. This patent illustrates the use of pesticide precursor compositions comprising bran from a mustard of the genus *Brassica*.

U.S. Pat. No. 5,757,100 to Martinez is titled Method and Material for Repelling Pests from Agricultural Crops. This patent teaches the use of natural components to protect crops organically. A combination of red pepper, garlic and black pepper is taught to repel undesirable pests.

U.S. Pat. No. 6,855,351 to Ramarethinam is titled Pesticide Formulation Containing Azadirachtin (Not Less than 300 PPM) and Salanin in Formulated Product with Neem Oil. This patent is another example of a pesticide, and shows a particular process for making the specified pesticide.

U.S. Pat. No. 7,019,036 to Hiromoto is titled Environmentally Friendly Pesticide Compositions. This patent claims to describe a minimum risk pesticide (in particular, a nematocide).

U.S. Pat. No. 7,029,687 to Joiner is titled Non Toxic Fire Ant and Termite Pesticide. In this patent, sulfur well water is taught to be mixed with seven edible ingredients to form a pesticide that is lethal to fire ant and termites.

While each of these patents describes products and processes that are useful for their intended purposes, each is not fully applicable to the objects of the present invention.

It is an object of the present invention to be dispensed in power and/or other forms.

It is a further object of the present invention to be an organic pesticide that is suitable for use in organic gardening.

It is a still further object of the present invention to be a bio-pesticide that attacks non-flying insects and larvae. In particular, it is desirable to control mealy bugs, aphids, spider mites and slugs.

It is a still further object yet of the present invention to break down in a timely manner, wherein toxicity does not accumulate in an unintended manner.

It is a still further object of the present invention to control pests by attacking multiple pest functions, and in particular through repellency, digestive inhabitancy, paralysis and suffocation.

Related, it is a still further object of the present invention to provide a pesticide that prevents and/or delays resistance of the pests to the pesticide.

Thus there exists a need for a bio-pesticide that solves these and other problems.

SUMMARY OF THE INVENTION

The present invention relates to a bio-pesticide comprising a mixture of natural spices that kills insects through direct contact.

In a preferred embodiment, the following constituents (with common names in parenthesis) are mixed with potting soil:

*Piper Nigrum* (Black Indian Pepper)
*Cuminum Cyminum* (Cumin)
*Cinnamomum Verum* (Cinnamon)
*Allium Sativum* (Garlic)

*Coriandrum Sativum* (Cilantro)
*Curcuma* (Turmeric)
*Foeniculum Vulgare* (Fennel)
*Trigonella Foenum Graecum* (Fenugreek)
*Syzygium Aromaticum* (Cloves)
*Capsicum* (Chili)
*Zingiber Officinale* (Ginger)
*Murraya koenigii* (Curry Tree or Sweet Neem Leaf)
*Brassica Nigra* (Black Mustard)
Sodium Chloride (Salt)

While each of these ingredients has individual qualities and properties, the mixture of these ingredients have been found to have synergistic advantages and effects.

In particular, the *Piper Nigrum, Cuminum Cyminum* and *Brassica Nigra* work together to attack the respiratory systems of insects by significantly increasing the rate of $CO_2$ production and thus induce suffocation.

The *Cinnamomum Verum, Foeniculum Vulgare* & *Capsicum* all attack the insect's digestive ability by its action as an ion channel-type receptor.

The *Allium Sativum, Coriandrum Sativum* & *Capsicum* operate in concert to repel insect activity mainly due to the presence of diallyl trisulfide which has a repulsive effect upon many insect species.

The *Coriandrum Sativum, Curcuma, Trigonella Foenum Graecum* & *Syzygium Aromaticum* cause paralysis in the insect through the presence of linalool.

The *Murraya koenigii* acts to inhibit the feeding activity of insects and doubles as a growth inhibitor this is primarily due to the presence of triterpenoid compounds which metabolize to indole alkaloids in the insect.

Accordingly, the botanical constituents all concert to work in synergism as a most effective bio-pesticide through several paths or modes of operation; repellency, digestive inhibitancy, paralysis and suffocation. Ingestion, repellency and digestive disruption are the initial frontline defenses and those insect species which are immune to these defenses then face paralysis as the secondary line of defense and finally those species which are not fully deterred by the above face certain extinction with the final and most formidable line of defense: suffocation. Employing multiple modes of operation advantageously is shown effective at preventing and/or delaying pest resistance to the pesticide. It has been observed that the present invention results in killing of the insects within 48-72 hours.

According to another advantage of the present invention, the formulation of the present invention falls squarely within the EPA guidelines on bio-pesticides which states that they "include naturally occurring substances that control pests (biochemical pesticides), microorganisms that control pests (microbial pesticides), and pesticidal substances produced by plants containing added genetic material (plant-incorporated protectants) or PIPs.

According to a still further advantage of the present invention, the toxicity of the present invention is restricted to insects, and is safe for humans at the intended application rates.

According to a still further advantage yet of the present invention, it washes off if sprayed with water and deteriorates quickly in soil leaving no harmful chemical residue.

According to a still further advantage yet of the present invention, the mixture is well suited for easy application, such as via dusting. The present invention can also be spayed or applied in a liquid form.

According to a still further advantage yet of the present invention, increased yields are achievable because of the effectiveness at controlling pests. In testing, new growth of plants has been observed within 10-14 days of use.

Other advantages, benefits, and features of the present invention will become apparent to those skilled in the art upon reading the detailed description of the invention.

BRIEF DESCRIPTION OF THE DRAWINGS

There are no formal drawings within this specification.

DETAILED DESCRIPTION OF THE PREFERRED EMBODIMENTS

While the invention will be described in connection with one or more preferred embodiments, it will be understood that it is not intended to limit the invention to those embodiments. On the contrary, it is intended to cover all alternatives, modifications and equivalents as may be included within the spirit and scope of the invention as defined by the appended claims.

According to the present invention, the following constituents or items can be mixed to produce a mixture of the present invention. It is understood that in the preferred embodiment, each constituent is finely ground.

A preferred embodiment of the present can be produced by producing a mixture having the following percentages. It is appreciated that these percentages do not reflect an amount of potting soil or other items that could be mixed with the mixture without departing from the broad aspects of the present invention.

| | |
|---|---|
| *Piper Nigrum* - | 25.75% |
| *Cuminum Cyminum* | 15.45% |
| *Cinnamomum Verum* | 11.05% |
| *Allium Sativum* | 12.03% |
| *Coriandrum Sativum* | 12.80% |
| *Curcuma* | 7.44% |
| *Foeniculum Vulgare* | 2.37% |
| *Trigonella Foenum Graecum* | 3.65% |
| *Syzygium Aromaticum* | 2.58% |
| *Capsicum* | 1.38% |
| *Zingiber Officinale* | 3.36% |
| *Murraya koenigii* | 1.60% |
| *Brassica Nigra* | 0.37% |
| Sodium Chloride | 0.17% |

In the preferred embodiment, and as seen in the following example, the mixture is mixed with a predetermined amount of potting soil for application It is appreciated that the percentages illustrated are not absolute, and may vary without departing from the broad aspects of the present invention.

Turning now to the next chart, a preferred recipe is shown for making a 2.0 kilogram amount a preferred embodiment of the present invention in a dusting form.

| | | |
|---|---:|---:|
| Indian Black Pepper Powder (*Piper Nigrum*) | 416.4 g | 20.8% |
| Curry Leaves (*Murraya koenigii*) | 26 g | 1.3% |
| Cumin Powder (*Cuminum Cyminum*) | 249.2 g | 12.5% |
| Cinnamon Powder (*Cinnamomum Verum*) | 178.3 g | 8.9% |
| Garlic Powder (*Allium Sativum*) | 194 g | 9.7% |
| Coriander Powder (*Coriandrum Sativum*) | 208 g | 10.4% |
| Turmeric Powder (*Curcuma*) | 120 g | 6% |
| Fenugreek Powder (*Trigonella Foenum-graecum*) | 58.5 g | 2.9% |
| Clove Powder (*Syzygium Aromaticum*) | 41.8 g | 2.1% |
| Red Chili (*Capiscum*) | 22.3 g | 1.2% |
| Ginger Powder (*Zingiber Officinale*) | 54.3 g | 2.79% |
| Fennel Powder (*Foeniculum Vulgare*) | 38.3 g | 1.9% |
| Salt (Sodium Chloride) | 2.8 g | .1% |

| | | |
|---|---|---|
| Mustard Seed (*Brassica Negra*) | 6 g | .3% |
| Potting Soil | 384.4 g | 19.2% |

Turning now to the individual operation of the constituent ingredients, the following is observed.

*Piper Nigrum* is commonly known as Indian Black Pepper. *Piper Nigrum* has appreciable amounts of piperine, which is an alkaloid and is irritating to the digestive tracts of most insects.

*Cuminum Cyminum* is commonly known as Cumin. The Cumin suffocates and inhibits the various biosynthetic processes of insects. The cumaldehyde is an alkaloid which is a naturally occurring organic compound.

*Cinnamomum Verum* commonly known as cinnamon. Cinnamon contains the organic compounds cinnamaldehyde, cinnamyl acetate, anethole and eugenol. These naturally occurring compounds possess insect antifeedant properties in which the insect is discouraged from eating.

*Allium Sativum* is commonly known as Garlic. Garlic is rich in diallyl disulfide, which acts both as an insect repellant and is observed to have some limited toxic properties against the same.

*Coriandrum Sativum* is commonly known as Cilantro. A major constituent of Cilantro is Linalool, which is a naturally occurring terpene alcohol. This compound demonstrates moderately effective action as a repellant and as paralyzing agent to insects.

*Curcuma* is commonly known as Turmeric. Turmeric contains a polyphenol known as *curcumin*. Curcumin acts as a paralyzing agent to the insect and is also effective as a repellant.

*Foeniculum Vulgare* is commonly known as Fennel. Fennel contains Anethole, which is an aromatic compound in the phenylpropanoid family. It acts to prevent the insect from digesting the food and causes oxidative stress.

*Trigonella Foenum Graecum* is commonly known as Fenugreek. Fenugreek contains saponin, which has a highly toxic paralyzing effect on insects.

*Syzygium Aromaticum* is commonly known as Cloves. Cloves contain Eugenol which a member of the phenylpropanoids family. This organic compound is effective in attacking the central nervous system of the insect and this results in paralysis and death.

*Capsicum* is commonly known as Chili. Chili is rich in capsaicin, which is in the amide family. *Capsaicin* causes irritation in the digestive tracts of insects and is primarily effective as a repellant.

*Zingiber Officinale* is commonly known as Ginger. Ginger has zingerone, shogaols and gingerols as its primary chemical compounds. Its primary purpose is as a repellent.

*Murraya koenigii* is commonly known as the Curry Tree or Sweet Neem Leaf. It acts as an insect feeding and growth inhibitor.

*Brassica Nigra* is commonly known as Indian Black Mustard. *Brassica Nigra* contains significant amounts of the chemical known as glucosinolate sinigrin, which is a naturally occurring organic compound that has effectiveness against phytophagus insects other pests by attacking their respiratory functions. The glucosinolate however, possesses limited biological activity until they are hydrolyzed.

Sodium Chloride is commonly known as salt. Its purpose in the formulation is as an inexpensive dessicant.

Targeted systems and processes of the above constituents are summarized in the following chart.

| Bio-pesticide Name | Class of Bio-pesticide | Targeted system/ Process | Mode of Action |
|---|---|---|---|
| Piperine | Botanical from *Piper Nigrum* | Metabolic Processes | Feeding Deterrent |
| Cumaldehyde | Botanical from *Cuminum Cyminum* | Metabolic Processes | Membrane Disruption |
| Anethol | Botanical from *Cinnamomum Verum* | Growth & Development Metabolic Processes | Prothoracicotropic hormone (PTTH) inhibitor; Phagostimulant disruptor |
| Diallyl Sulfide | Botanical from *Allium Sativum* | Metabolic Processes | Feeding Deterrent |
| Linalool | Botanical from *Coriandrum Sativum* | Nervous System | Sodium Channel Modulator |
| Curcumin | Botanical from *Curcuma* | Nervous System | Channel Modulator |
| Saponin | Botanical from *Trigonella Foenum Graecum* | Metabolic Processes | Membrane Disruption |
| Eugenol | Botanical from *Cinnamomum Verum* | Metabolic Processes | Feeding Deterrent |
| Capsaicin | Botanical from *Capsicum* | Metabolic Processes | Feeding Deterrent |
| Zingerol | Botanical from *Zingiber Officinale* | Metabolic Processes | Feeding Deterrent |
| Azadirachtin | Botanical from *Murraya koenigil* | Growth & Development Metabolic Processes | Prothoracicotropic hormone (PTTH) inhibitor; Phagostimulant disruptor |
| Glucosinate Sinigrin | Botanical from *Brassica Nigra* | Metabolic Processes | Membrane Disruption |
| Cinnamaldehyde | Botanical from *Cinnamomum Verum* | Energy Production | Interference with glucose uptake or utilization |

The ingredients listed above combine in a synergistic manner to comprise a more effective insecticide than any one of the individual components.

In particular:

*Piper Nigrum*, *Cuminum Cyminum* and *Brassica Nigra* work together to attack the respiratory systems of insects by significantly increasing the rate of $CO_2$ production and thus induce suffocation.

*Cinnamomum Verum*, *Foeniculum Vulgare* and *Capsicum* attack the insect's digestive ability by its action as an ion channel-type receptor.

*Allium Sativum*, *Coriandrum Sativum* and *Capsicum* operate in concert to repel insect activity mainly due to the presence of diallyl trisulfide which has a repulsive effect upon many insect species.

*Coriandrum Sativum*, *Curcuma*, *Trigonella Foenum Graecum* and *Syzygium Aromaticum* cause paralysis in the insect through the presence of linalool.

*Murraya koenigii* acts to inhibit the feeding activity of insects and doubles as a growth inhibitor this is primarily due to the presence of triterpenoid compounds which metabolize to indole alkaloids in the insect.

The botanical constituents all concert to work in synergism as a most effective bio-pesticide through several paths; repellency, digestive inhabitancy, paralysis and suffocation. Ingestion, repellency and digestive disruption are the initial frontline defenses and those insect species which are immune to these defenses then face paralysis as the secondary line of defense and finally those species which are not fully deterred by the above face certain extinction with the final and most formidable line of defense: suffocation.

*Allium Sativum, Coriandrum Sativum* and *Capsicum* work together as the initial defense against insect attack. The constituents diallyl sulfide and capsaicin have complimentary activity.

*Coriandrum Sativum, Curcuma, Trigonella Foenum Graecum* and *Syzygium Aromaticum* cause paralysis through the activity of linalool.

*Piper Nigrum, Cuminum Cyminum* and *Brassica Nigra* contain piperine, cumaldehyde and glucosinolate sinigrin respectively.

The formulation of the present invention falls squarely within the EPA guidelines on bio-pesticides which states that they "include naturally occurring substances that control pests (biochemical pesticides), microorganisms that control pests (microbial pesticides), and pesticidal substances produced by plants containing added genetic material (plant-incorporated protectants) or PIPs."

The toxicity of constituents of the present invention is restricted to insects and non mammalian toxicity has not been observed.

Turning now to the effectiveness of the present invention, it has been observed that in a direct contact mode of operation, that the bio-pesticide kills insects within 48-72 hrs. It washes off if sprayed with water and deteriorates quickly in soil leaving no harmful chemical residue. It is preferred that the mixture of the present invention is applied to the top of leaves and buds of plants, and also around the base of plants. It has been observed that new growth of plants can be seen in 10-14 days. Reapplication of the present invention can be made after 21 days, as necessary, to control pest population.

It is preferred that the user wear gloves and protective clothing, and take measures to keep the present invention out of face and eyes during application, as it will cause irritation to eyes upon contact, cause irritation to the lungs if inhaled directly, and cause irritation to open wounds.

It is preferred that approximately 100-500 grams of the mixture of the present invention be applied per square meter. Yet, it is understood that a more aggressive application rate may be applied for severe cases. It is further preferred that the mixture should be applied to the tops of leaves, buds of the plants, and also around the base of plants. Watering of the plants should preferably be avoided after dusting of the plants until next day or 24 hours later.

The present invention has been observed to be effective against: Mealy Bugs, Aphids Spider Mites, Slugs and Phytophthora Disease.

The present invention can be used in organic gardens, and on fruits and vegetables, such as tomatoes, peppers melons, carrots, broccoli, lettuce, onions, apples, and coconut and date palms. In addition to annual and perennial bedding plants, flowers, roses, potted plants, foliage plants, trees, shrubs, and grass located in residential greenhouses and residential and commercial landscapes. It is made up of natural plant material and is safe to use on any fruits or vegetables up to and including the same day of harvest.

In a laboratory test, a 10% by weight slurry of the bio-pesticide in de-ionized water was prepared and its pH was determined with an Orion Model 720A pH meter. The pH of the slurry was found to be 5.56 (pH of DI Water was about 6.5) indicating that the material is slightly acidic in water.

In further laboratory tests, the solubility of the bio-pesticide in de-ionized water at room temperature was measured. To accomplish this, a slurry was prepared by adding 0.3 grams of the sample to 20 ml of de-ionized water. The water was removed by filtration and the remaining solids were dried at room temperature (about 21° C.) and weighed. The amount of water soluble substances in the bio-pesticide was found to be 30.6% by weight.

It is understood that while the present invention has been described with respect to a dusting application, that it may be applied in other forms without departing from the broad aspects of the present invention. For example, the mixture could be liquefied or suspended in a liquid form and sprayed onto plants.

Thus it is apparent that there has been provided, in accordance with the invention, a bio-pesticide and methods of making and using the same that fully satisfies the objects, aims and advantages as set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A bio-pesticide composition consisting essentially of:
*Piper nigrum* in an amount of 20-30%;
*Cuminum cyminum* in an amount of 10-20%;
*Cinnamomum verum* in an amount of 5-15%;
*Allium sativum* in an amount of 5-20%;
*Coriandrum sativum* in an amount of 5-20%;
*Curcuma* in an amount of 3-15%;
*Foeniculum vulgare* in an amount of 0.01-10%;
*Trigonella foenum graecum* in an amount of 0.01-10%;
*Syzygium aromaticum* in an amount of 0.01-10%;
*Capsicum* in an amount of 0.01-10%;
*Zingiber officinale* in an amount of 0.1-10%;
*Murraya koenigii* in an amount of 0.01-5%; and
*Brassica nigra* in an amount of 0.01-5%, wherein said *Piper nigrum, Cuminum cyminum, Cinnamomum verum, Allium sativum, Coriandrum sativum, Curcuma, Foeniculum vulgare, Trigonella foenum graecum, Syzygium aromaticum, Capsicum, Zingiber officinale, Murraya koenigii* and *Brassica nigra* are in powder form, and wherein the bio-pesticide composition is a dust that is applied to an area in need of treatment at a rate of approximately 100-500 grams of bio-pesticide composition per square meter.

2. The bio-pesticide composition of claim 1, further consisting of sodium chloride, and wherein:
the *Piper nigrum* is present in an amount of approximately 25.75%;
the *Cuminum cyminum* is present in an amount of approximately 15.45%;
the *Cinnamomum verum* is present in an amount of approximately 11.05%;
the *Allium sativum* is present in an amount of approximately 12.03%;
the *Coriandrum sativum* is present in an amount of approximately 12.80%;
the *Curcuma* is present is present in an amount of approximately 7.44%;
the *Foeniculum vulgare* is present in an amount of approximately 2.37%;
the *Trigonella foenum graecum* is present in an amount of approximately 3.65%;
the *Syzygium aromaticum* is present in an amount of approximately 2.58%;

the *Capsicum* is present in an amount of approximately 1.38%;

the *Zingiber officinale* is present in an amount of approximately 3.36%;

the *Murraya koenigii* is present in an amount of approximately 1.60%;

the *Brassica nigra* is present in an amount of approximately 0.037%; and the sodium chloride is present in an amount of approximately 0.17%.

3. The bio-pesticide composition of claim 1, wherein the bio-pesticide composition is mixed with potting soil.

4. The bio-pesticide composition of claim 1 wherein said bio-pesticide kills pests within 72 hours.

* * * * *